United States Patent [19]

Prince et al.

[11] 4,051,148

[45] Sept. 27, 1977

[54] 6,11-DIHYDRODIBENZO-[b.e.]-THIEPIN-11-ONE-3-CARBOXALDEHYDE

[75] Inventors: Anthony Prince, Mountain View; Otto Halpern; Jack Ackrell, both of Palo Alto, all of Calif.

[73] Assignee: Syntex (U.S.A.) Inc., Palo Alto, Calif.

[21] Appl. No.: 697,648

[22] Filed: June 18, 1976

[51] Int. Cl.$^2$ .......................................... C07D 337/12
[52] U.S. Cl. .................................................. 260/327 B
[58] Field of Search ............... 260/327 B, 333, 515 R, 260/517

[56] References Cited

U.S. PATENT DOCUMENTS

| 3,975,431 | 8/1976 | White | 260/515 R |
|---|---|---|---|
| 3,987,094 | 10/1976 | White | 260/515 R |
| 3,989,839 | 11/1976 | Ackrell | 424/275 |
| 3,994,964 | 11/1976 | White | 260/515 R |

Primary Examiner—Cecilia M. S. Jaisle
Attorney, Agent, or Firm—Gerard A. Blaufarb; William B. Walker

[57] ABSTRACT

This invention relates to a novel method for the preparation of 6,11-dihydrodibenzo-[b.e.]-thiepin-11-one-3-acetic acid and the novel intermediate 6,11-dihydrodibenzo-[b.e.]-thiepin-11-one-3-carboxaldehyde used in the preparation thereof.

1 Claim, No Drawings

6,11-DIHYDRODIBENZO-[b.e.]-THIEPIN-11-ONE-3-CARBOXALDEHYDE

This invention relates to a novel method for the preparation of 6,11-dihydrodibenz-[b.e.]-thiepin-11-one-3-acetic acid, which compound is disclosed in copending U.S. application Ser. No. 634,086, filed Nov. 21, 1975, U.S. Pat. No. 4,000,308, and to the novel intermediate 6,11-dihydrodibenzo-[b.e.]-thiepin-11-one-3-carboxaldehyde in the preparation thereof, according to the following reaction sequence:

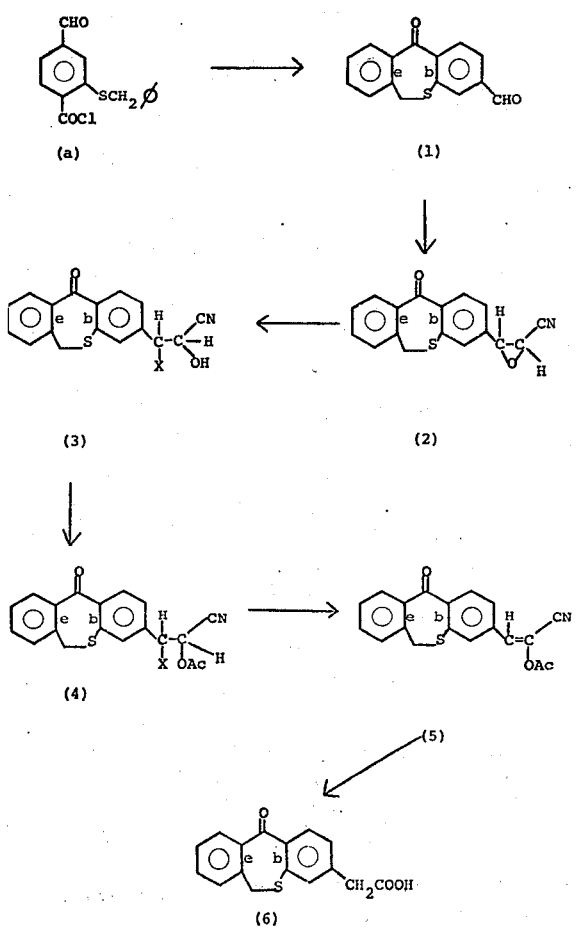

wherein φ is phenyl, Ac is acyl containing from 2 to 5 carbon atoms, and X is halo (bromo, chloro, fluoro or iodo).

The compound of formula (a), 3-benzylmercapto-4-chlorocarbonyl benzaldehyde, prepared according to the procedure set forth in the Preparation below, is cyclized with a Lewis acid, e.g., aluminum trichloride, stannic chloride, boron trifluoride, and the like, in the presence of an inert organic solvent, e.g., nitromethane, nitrobenzene, nitrotoluene, methylene, chloride, chloroform, carbon tetrachloride, dichloroethane, and the like, or mixtures thereof, at a temperature of from about 0° to about 40° C, for from about 5 minutes to about 3 hours, preferably from about 15° to about 20° C, for from about 10 minutes to about 2 hours, to obtain the novel non-pharmaceutical intermediate compound of formula (1), 6,11-dihydrodibenzo-[b.e.]-thiepin-11-one-3-carboxaldehyde.

The novel intermediate compound of formula (1) is then treated with an alkylating agent, e.g., chloroacetonitrile, bromoacetonitrile or iodoacetonitrile, and an organic base, e.g., sodium methoxide, potassium methoxide, sodium t-amylate, or an inorganic base, e.g., sodium hydroxide, potassium hydroxide, and the like, in the presence of an inert organic solvent, e.g., tetrahydrofuran, toluene, benzene, and the like, for from about 0° to 25° C, from about 15 minutes to about 2-3 hours, preferably from about 5° to about 10° C, for from about 30 minutes to about 1 hour, to obtain the compound of formula (2), 3-(6,11-dihydrodibenzo-[b.e.]-thiepin-11-one-3-yl)glycidonitrile.

The epoxy ring of the compound of formula (2) is then opened by treatment with a hydrogen halide, e.g., hydrogen bromide, hydrogen chloride, hydrogen fluoride, or hydrogen iodide, in the presence of an organic acid, e.g., acetic acid propionic acid, or in an inert solvent, e.g., ether, toluene, benzene, and the like, at a temperature of from about 15° to about 25° C, for from about 5 minutes to about 1 hour, preferably from about 15° to about 20° C, for from about 30 to about 45 minutes, to obtain the compound of formula (3), 3-(6,11-dihydrodibenzo-[b.e.]-thiepin-11-one-3-yl)-2-hydroxy-3-halopropionitrile.

The compound of formula (3), is then treated with an acylating agent containing from 2 to 5 carbon atoms, preferably an acid anhydride, e.g., acetic anhydride, propionic anhydride and the like, in the presence of an organic base, e.g., pyridine, collidine, triethylamine, and the like, in an inert organic solvent, e.g., toluene, benzene, and the like, at a temperature of from about 10° to about 100° C, for from about 5 minutes to about 2 hours, preferably from about 15° to about 20° C, for from about 1 to 2 hours, to obtain the compounds of formula (4), 3-(6,11-dihydrodibenzo-[b.e.]-thiepin-11-one-3-yl)-2-acyloxy-3-halopropionitrile.

A compound of formula (4) is then dehydrohalogenated with an organic base, e.g., triethylamine, pyridine, and the like, in an inert organic solvent, e.g., toluene, benzene, and the like, at a temperature of from about 10° to about 30° C, for from about 30 minutes to about 3 hours, preferably from about 15° to about 20° C, for from about 1 to about 2 hours, to obtain a compound of formula (5), 3-(6,11-dihydrodibenzo-b,e.]-thiepin-11-one-3-yl)-2-acyloxyacrylonitrile.

A compound of formula (5) is then hydrolyzed with a base, preferably an inorganic base, e.g., sodium hydroxide, potassium, hydroxide, and the like, in the presence of water and an inert organic solvent, e.g., tetrahydrofuran, and the like, or with sodium hydroxide, potassium hydroxide, in a polar protic solvent e.g., methanol, ethanol, and the like, at a temperature of from about 10° to about 50° C, for from about 1 to about 5 hours, preferably from about 15° to about 20° C, for from about 1 to about 2 hours, to obtain the compound of formula (6), 6,11-dihydrodibenzo-[b.e.]-thiepin-11-one-3-acetic acid.

Alternatively, a compound of formula (5) can be hydrolyzed to the compound of formula (6) using a mineral acid, e.g., hydrochloric acid, sulfuric acid, perchloric acid, and the like, preferably concentrated hydrochloric acid, in an organic solvent, e.g., dioxane, tetrahydrofuran, monoglyme, methanol, and the like, at a temperature of from about 50° to about 100° C, for from about 2 to about 6 hours, preferably at a temperature of from about 60° to about 80° C for from about 2 to about 4 hours.

It is to be understood that isolation of the compounds described herein can be effected, if desired, by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the Preparation and Examples herein below. However, other equivalent separation or isolation procedures could, of course, also be used.

By the term room temperature is meant a temperature of from about 15° to about 25° C.

A further understanding of the invention can be had from the following non-limiting Preparation and Examples.

PREPARATION

A. 1.0 Kg. of fuming sulfuric acid is added dropwise to 500 g of nitroterephthalic acid in 2.5 liters of methanol and the so lution is refluxed for 4 hours. The reaction mixture is cooled to room temperature and cautiously diluted up to 10 liters with water. The solid is filtered, washed to neutrality with water and dried in vacuo at 40°-45° C to yield 550 g of nitroterephthalic acid dimethyl ester having a melting point of 72.5°-74.5° C.

B. A solution of 747 g of nitroterephthalic acid ester in 3 liters of dimethylformamide is added to a slurry of 82 g of 100% sodium hydride and 405 ml of benzyl mercaptan in 3 liters of dimethylformamide at −30° C. The reaction mixture is stirred for 1 hour at −20° C and 1 hour at 0° C. Water (6 lliters) is added slowly yielding a slurry which is then poured into 20 liters or water, filtered, washed well with water and dried in vacuo to yield 826 g of benzylmercapto terephthalic acid dimethyl ester having a melting point of 90°-93.5° C.

C. 50G of benzylmercapto terephthalic acid dimethyl ester is suspended in a solution of 750 ml of methanol to which is added 200 ml of a solution of 15 g of sodium carbonate monohydrate in 350 ml of water. The reaction mixture is refluxed for 30 minutes, cooled and diluted with 750 ml of water. The solid is filtered and resuspended in 375 ml of methanol and 100 ml of the above sodium carbonate solution, refluxed 30 minutes, cooled, 375 ml of water is added thereto, filtered and the damp cake resuspended in 187 ml of methanol. The remaining 50 ml of the sodium carbonate solution is then added and the reflux process repeated. The combined aqueous filtrates are acidified with 50 ml of conentrated hydrochloric acid yielding a precipitate which is filtered, washed with water and the damp cake is dissolved in ethyl acetate. The ethyl acetate solution is washed with water, dried over sodium sulfate and evaporated to yield 46 g of crude 3-benzylmercapto-4-carbomethoxy benzoic acid, which is used without further purification in part D.

D. 28 ml of boron trifluoride etherate is added to a suspension of 46 g of crude 3-benzylmercapto-4-carbomethoxy benzoic acid in 750 ml of anhydrous tetrahydrofuran and 7 g of sodium borohydride. The reaction mixture is stirred for 3-4 hours at room temperature, then diluted with about 20 ml of 2N hydrochloric acid and 500 ml of water. The product obtained is extracted with ether and the ether extract is washed with water and saturated sodium chloride solution, dried over sodium sulfate and evaporated to dryness. Crystallization from ethyl acetate:hexane (1:2) yielded 28.6 g of 3-benzylmercapto-4-carbomethoxy benzyl alcohol having a melting point of 89.5°-92° C.

E. A solution of 30 g 3-benzylmercapto-4-carbomethoxy benzyl alcohol in 900 ml of methylene chloride is stirred with 60 g of Florisil (activated magnesium silicate) in 900 ml of methylene chloride. To the thus-obtained slurry is added 39 g of solid pyridinium chlorochromate and the black reaction mixture obtained is stirred for 3-4 hours at room temperature, filtered over Celite (diatomaceous earth), and washed with 600 ml of methylene chloride. The methylene chloride filtrate is stirred overnight with a solution of 14 g of potassium hydroxide in 500 ml of water which removes all the dark color from the organic layer. The methylene chloride layer is separated, washed with 100 ml of 2N hydrochloric acid and then with 300 ml of water, dried over sodium sulfate and evaporated to dryness to yield 27.5 g of 3-benzylmercapto-4-carbomethoxy benzaldehyde having a melting point of 91°-93° C.

F. To a boiling solution of 27.5 g of 3-benzylmercapto-4-carbomethoxy benzaldehye in 250 ml of methanol is added a solution of 7 g of potassium hydroxide in 24 ml of water. The reaction mixture is refluxed for 3-4 hours, then water is added to a volume of 1 liter. 10 Ml of acetic acid is added and the thus-obtained slurry is cooled, filtered, washed with water and air-dried to yield 25 g of 3-benzylmercapto-4-carboxy benzaldehyde, a yellow powder, having a melting point of 182°-190° C.

G. To a solution containing 23.2 g of 3-benzylmercapto-4-carboxy benzaldehyde in 250 ml of methylene chloride is added 15 ml of thionyl chloride and 0.5 ml of dimethylformamide. The reaction mixture is refluxed for 6-7 hours, then evaporated to dryness. Crystallization from 100 ml of ether yielded 27.0 g of 3-benzylmercapto-4-chlorocarbonyl benzaldehyde (a).

EXAMPLE 1

A solution of 10g of 3-benzylmercapto-4-chlorocarbonyl benzaldehyde in 100 ml of methylene chloride is added at 10°-15° C over 1 hour to a solution of 15.0 g of anhydrous aluminum trichloride and 6.0 ml of nitromethane in 150 ml of methylene chloride. The reaction mixture is poured into 300 ml of ice cold 2N hydrochloric acid and stirred 30 minutes. The methylene chloride layer is washed with 200 ml of 2N hydrochloric acid, twice with 200 ml of water and twice with 200 ml of saturated sodium chloride. The aqueous layers are back extracted with two 100 ml portions of methylene chloride. The methylene chloride extracts are combined, dried over anhydrous sodium sulfate and evaporated to dryness to give 8.2 g of crude product which is slurried with ethyl acetate and filtered. The ethyl acetate filtrate is evaporated to dryness under vacuum and the residue is redissolved in methylene chloride and percolated over 56 g silica gel. Those fractions showing the presence of the cyclized aldehyde are combined, concentrated in vacuo and crystallized from ether to yield 5.5 g of 6,11-dihydrodibenzo-[b.e.]-thiepin-11-one-3-carboxaldehyde (1), having a melting point of 100.5°-103° C.

EXAMPLE 2

One gram of 6,11-dihydrodibenzo-[b.e.]-thiepin-11-one-3-carboxaldehyde (1) is dissolved in 40 ml. of tetrahydrofuran. The solution is cooled to 0° C and nitrogen bubbled through the solution for ten minutes. 0.5 Ml of chloroacetonitrile is then added, followed by the addition of 240 mg of powdered sodium methoxide. The reaction mixture is stirred for 45 minutes, acidified with acetic acid and evaporated to a small volume under vacuum. 20 Ml of water and 60 ml of ethyl acetate is added. The ethyl acetate extract is washed with water, dried over sodium sulfate and evaporated to dryness to yield about 1.1 g of crude product which is percolated over 10 gm of silica gel with methylene chloride to yield a purified product containing 3-(6,11-dihydrodibenzo-[b.e.]-thiepin-11-one-3-yl)-glycidonitrile (2).

EXAMPLE 3

The purified product containing 3-(6,11-dihydrodienzo-[b.e.]-thiepin-11-one-3-yl)-glycidonitrile (2), obtained in Example 2, is slurried with 10 ml of acetic acid. A solution of 1.2 ml of 30% hydrogen bromide in acetic acid is added and stirred for 15–30 minutes. The solution thus obtained is poured into 100 ml of water and the yellow precipitate which forms is filtered, washed with water and dried under vacuum to yield about 1.0 g of a residual product containing 3-(6,11-dihydrodibenzo-[b.e.]-thiepin-11-one-3-yl)-2-hydroxy-3-bromopropionitrile (3).

EXAMPLE 4

About 750 mg of 3-(6,11-dihydrodibenzo-[b.e.]-thiepin-11-one-3-yl)-2-hydroxy-3-bromopropionitrile (3), obtained in Example 3, is suspended in 10 ml of toluene. To the thus-obtained slurry there is added 1.1 equivalents each of acetic anhydride and pyridine and the reaction mixture is stirred at 10°–15° C for 1 to 1½ hours (monitoring the reaction mixture for complete actylation by thin layer chromatography) to yield a solution containing 3-(6,11-dihydrodibenzo-[b.e.]-thiepin-11-one-3-yl)-2-acetoxy-3-bromopropionitrile (4, Ac = acetyl).

EXAMPLE 5

To the solution containing 3-(6,11-dihydrodibenzo-[b.e.]-thiepin-11-one-3-yl)-2-acetoxy-3-bromopropionitrile (4, Ac = Acetyl), obtained in Example 4, is added 1.1 equivalents of triethylamine at room temperature. The reaction mixture is maintained at room temperature for 15 to 45 minutes (until dehydrobromination is complete) and the thus-obtained solution is poured into 50 ml of water and extracted with 50 ml of ethyl acetate. The ethyl acetate extract is washed with water, dried over sodium sulfate and evaporated to dryness to yield 0.6 g of an oily product containing 3-(6,11-dihydrodibenzo-[b.e.]-thiepin-11-one-3-yl)-2-acetoxyacrylonitrile (5, Ac = acetyl).

EXAMPLE 6A

The product containing 3-(6,11-dihydrodibenzo-[b.e.]-thiepin-11-one-3-yl)-2-acetoxyacrylonitrile (5, Ac = acetyl), obtained in Example 5, is treated with 20 ml of a dilute solution of sodium hydroxide in 20 ml of tetrahudrofuran at room temperature for 2–3 hours. The tetrahydrofuran is evaporated under vacuum, 60 ml of water is added and the mixture is extracted with 50 ml of ethyl acetate. The aqueous layer is acidified with 2N hydrochloric acid and extracted with 50 ml of ethyl acetate. The ethyl acetate extract is evaporated and the residue thus obtained is crystallized from ether to yield about 410 mg of a product, 100 mg of which is percolated over silica and the thus purified fractions are combined, evaporated to dryness and crystallized from benzene solution to yield 6,11-dihydrodibenzo-[b.e.]-thiepin-11-one-3-acetic acid (6) having a melting point of 156°–157° C.

EXAMPLE 6B 1.5 G of 3-(6,11-dihydrodibenzo-b.e.]-thiepin-11-one-3-yl)-2-acetoxyacrylonitrile (5, Ac=acetyl) is dissolved in 12 ml of dioxane and to the solution is added 2.0 ml of concentrated hydrochloric acid. The reaction mixture is heated at 65°–75° C, with stirring for 4 hours (thin layer chromatography indicating the absence of starting material). The reaction mixture is poured into 150 ml of water and extracted with 60 ml of ethyl acetate. The ethyl acetate solution is washed once with 50 ml of water and once with 50 ml of brine. The aqueous washings are re-extracted with 30 ml of ethyl acetate. The ethyl acetate extracts are combined, dried over anhydrous sodium sulfate, and evaporated to dryness to give a residue. Crystallization of the residue from benzene yielded a first crop (0.7 g) of 6,11-dihydrodibenzo-[b.e.]-thiepin-11-one-3-acetic acid (6) having a melting point of 153°–155° C; and another crystallization from benzene gives material having a melting point of 156°–157° C.

What is claimed is:
1. 6,11-dihydrodibenzo-[b.e.]-thiepin-11-one-3-carboxaldehyde.

* * * * *